(12) United States Patent
Wynn et al.

(10) Patent No.: US 8,066,974 B2
(45) Date of Patent: Nov. 29, 2011

(54) CONTRAST AGENTS

(75) Inventors: Duncan Wynn, Amersham (GB); Harry John Wadsworth, Herts (GB); Ian Martin Newington, Amersham (GB)

(73) Assignee: GE Healthcare AS, Oslo (NO)

( * ) Notice: Subject to any disclaimer, the term of this patent is extended or adjusted under 35 U.S.C. 154(b) by 473 days.

(21) Appl. No.: 12/299,794

(22) PCT Filed: May 10, 2007

(86) PCT No.: PCT/NO2007/000168
§ 371 (c)(1),
(2), (4) Date: Nov. 6, 2008

(87) PCT Pub. No.: WO2007/133088
PCT Pub. Date: Nov. 22, 2007

(65) Prior Publication Data
US 2009/0136425 A1    May 28, 2009

(30) Foreign Application Priority Data

May 11, 2006   (NO) .................................. 20062119

(51) Int. Cl.
*A61K 49/04*    (2006.01)
(52) U.S. Cl. ..................... 424/9.451; 424/1.65; 424/9.1; 424/9.452; 424/9.454; 424/9.6; 564/47; 564/133; 564/152; 564/153; 560/26; 514/591; 514/616

(58) Field of Classification Search ....................... None
See application file for complete search history.

(56) References Cited

U.S. PATENT DOCUMENTS 4,109,081 A * 8/1978 Smith ............................. 536/53
5,817,873 A   10/1998 Meyer et al.

FOREIGN PATENT DOCUMENTS

EP   0782563    7/1997
WO   95/01966   1/1995

OTHER PUBLICATIONS

PCT/NO2007/000168 Int'l Search Report/Written Opinion dated Sep. 2007.

* cited by examiner

*Primary Examiner* — Porfirio Nazario Gonzalez
*Assistant Examiner* — Yate K Cutliff

(57) ABSTRACT

The present invention relates to a class of compounds and to diagnostic compositions containing such compounds where the compounds are iodine containing compounds. More specifically the iodine containing compounds are chemical compounds containing an aliphatic central moiety containing urea or urethane functions allowing for the arrangement of three iodinated phenyl groups bound thereto. The invention also relates to the use of such diagnostic compositions as contrast agents in diagnostic imaging and in particular in X-ray imaging and to contrast media containing such compounds.

20 Claims, No Drawings

CONTRAST AGENTS

This application is a filing under 35 U.S.C. 371 of international application number PCT/NO2007/000168, filed May 10, 2007, which claims priority to application number 20062119 filed May 11, 2006, in Norway the entire disclosure of which is hereby incorporated by reference.

TECHNICAL FIELD OF THE INVENTION

The present invention relates to a class of compounds and to diagnostic compositions containing such compounds where the compounds are iodine containing compounds. More specifically the iodine containing compounds are chemical compounds containing an aliphatic central moiety containing urea or urethane functions allowing for the arrangement of three iodinated phenyl groups bound thereto.

The invention also relates to the use of such diagnostic compositions as contrast agents in diagnostic imaging and in particular in X-ray imaging and to contrast media containing such compounds.

DESCRIPTION OF RELATED ART

All diagnostic imaging is based on the achievement of different signal levels from different structures within the body. Thus in X-ray imaging for example, for a given body structure to be visible in the image, the X-ray attenuation by that structure must differ from that of the surrounding tissues. The difference in signal between the body structure and its surroundings is frequently termed contrast and much effort has been devoted to means of enhancing contrast in diagnostic imaging since the greater the contrast between a body structure and its surroundings the higher the quality of the images and the greater their value to the physician performing the diagnosis. Moreover, the greater the contrast the smaller the body structures that may be visualized in the imaging procedures, i.e. increased contrast can lead to increased spatial resolution.

The diagnostic quality of images is strongly dependent on the inherent noise level in the imaging procedure, and the ratio of the contrast level to the noise level can thus be seen to represent an effective diagnostic quality factor for diagnostic images.

Achieving improvement in such a diagnostic quality factor has long been and still remains an important goal. In techniques such as X-ray, magnetic resonance imaging (MRI) and ultrasound, one approach to improving the diagnostic quality factor has been to introduce contrast enhancing materials formulated as contrast media into the body region being imaged.

Thus in X-ray early examples of contrast agents were insoluble inorganic barium salts which enhanced X-ray attenuation in the body zones into which they distributed. For the last 50 years the field of X-ray contrast agents has been dominated by soluble iodine containing compounds. Commercial available contrast media containing iodinated contrast agents are usually classified as ionic monomers such as diatrizoate (marketed e.g. under the trade name Gastrografen™), ionic dimers such as ioxaglate (marketed e.g. under the trade name Hexabrix™), nonionic monomers such as iohexyl (marketed e.g. under the trade name Omnipaque™), iopamidol (marketed e.g. under the trade name Isovue™), iomeprol (marketed e.g. under the trade name Iomeron™) and the non-ionic dimer iodixanol (marketed under the trade name and Visipaque™).

The most widely used commercial non-ionic X-ray contrast agents such as those mentioned above are considered safe. Contrast media containing iodinated contrast agents are used in more that 20 millions of X-ray examinations annually in the USA and the number of adverse reactions is considered acceptable. However, since a contrast enhanced X-ray examination will require up to about 200 ml contrast media administered in a total dose, there is a continuous drive to provide improved contrast media.

The utility of the contrast media is governed largely by its toxicity, by its diagnostic efficacy, by adverse effects it may have on the subject to which the contrast medium is administered, and by the ease of storage and ease of administration. Since such media are conventionally used for diagnostic purposes rather than to achieve direct therapeutic effect, it is generally desirable to provide media having as little as possible effect on the various biological mechanisms of the cells or the body as this will lead to lower toxicity and lower adverse clinical effect. The toxicity and adverse biological effects of a contrast medium are contributed to by the components of the formulation medium, e.g. the solvent or carrier as well as the contrast agent itself and its components such as ions for the ionic contrast agents and also by its metabolites.

The major contributing factors to the toxicity of the contrast medium are identified as the chemotoxicity of the contrast agent, the osmolality of the contrast medium and the ionic composition or lack thereof of the contrast medium.

Desirable characteristics of an iodinated contrast agent are low toxicity of the compound itself (chemotoxicity), low viscosity of the contrast medium wherein the compound is dissolved, low osmolality of the contrast medium and a high iodine content (frequently measured in g iodine per ml of the formulated contrast medium for administration). The iodinated contrast agent must also be completely soluble in the formulation medium, usually an aqueous medium, and remain in solution during storage.

The osmolalities of the commercial products, and in particular of the non-ionic compounds, is acceptable for most media containing dimers and non-ionic monomers although there is still room for improvement. In coronary angiography for example, injection into the circulatory system of a bolus dose of contrast medium has caused severe side effects. In this procedure contrast medium rather than blood flows through the system for a short period of time, and differences in the chemical and physiochemical nature of the contrast medium and the blood that it replaces can cause undesirable adverse effects such as arrhythmias, QT prolongation and reduction in cardiac contractive force. Such effects are seen in particular with ionic contrast agents where osmotoxic effects are associated with hypertonicity of the injected contrast medium. Contrast media that are isotonic or slightly hypotonic with the body fluids are particularly desired. Low osmolar contrast media have low renal toxicity which is particularly desirable. The osmolality is a function of the number of particles per volume unit of the formulated contrast medium.

To keep the injection volume of the contrast media as low as possible it is highly desirable to formulate contrast media with high concentration of iodine/ml, and still maintain the osmolality of the media at a low level, preferably below or close to isotonicity. The development of non-ionic monomeric contrast agents and in particular non-ionic bis(triiodophenyl) dimers such as iodixanol (EP patent 108638) has provided contrast media with reduced osmotoxicity allowing contrast effective iodine concentration to be achieved with hypotonic solution, and has even allowed correction of ionic imbalance by inclusion of plasma ions while still maintaining the contrast medium Visipaque™ at the desired osmolality (WO 90/01194 and WO 91/13636).

The X-ray contrast media at commercial high iodine concentration have relative high viscosity, ranging from about 15 to about 60 mPas at ambient temperature. Generally, contrast media where the contrast enhancing agent is a dimer has higher viscosity than the corresponding contrast media where the contrast enhancing agent is the monomer corresponding to the dimer. Such high viscosities may pose problems to the administrators of the contrast medium, requiring relatively large bore needles or high applied pressure, and are particularly pronounced in pediatric radiography and in radiographic techniques which require rapid bolus administration, e.g. in angiography.

X-ray contrast agents of high molecular weight has been proposed, e.g. polymers with substituted triiodinated phenyl groups grafted on the polymer, see EP 354836, EP 436316 and U.S. Pat. No. 5,019,370. Further, WO 9501966, EP 782563 and U.S. Pat. No. 5,817,873 read on compounds having e.g. 3 and 4 substituted triiodinated phenyl groups arranged linearly or around a central core. However, none of these proposed compounds are on the market.

Hence there still exists a desire to develop contrast agents that solves one or more of the problems discussed above. Such agents should ideally have improved properties over the soluble iodine containing compounds on the market in one or more of the following properties: renal toxicity, osmolality, viscosity, solubility, injection volumes/iodine concentration and attenuation/radiation dose.

SUMMARY OF THE INVENTION

The present invention provides contrast media having improved properties over the known media with regards to at least one of the following criteria osmolality (and hence the renal toxicity), viscosity, iodine concentration and solubility. The contrast media comprises iodine containing contrast enhancing compounds where iodine containing compounds are chemical compounds containing a central aliphatic moiety, allowing for the arrangement of three iodinated phenyl groups bound to thereto through linker groups containing urea functions. The iodine containing contrast enhancing compounds can be synthesized from commercially available and relatively inexpensive starting materials.

DETAILED DESCRIPTION OF THE INVENTION

The new compounds of the invention, their use as X-ray contrast agents, their formulation and production are specified in the attached claims and in the specification hereinafter.

The contrast enhancing compounds are synthetic chemical compounds of formula (I)

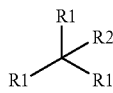

Formula (I)

wherein
each $R^1$ independently are the same or different and denote a moiety $-(CX_2)_n-R^3-R$;
$R^2$ denote hydrogen and $C_1$-$C_4$ alkyl where the alkyl group may be substituted by hydroxyl groups or interrupted by an oxygen atom;

each $R^3$ independently are the same or different and denote a moiety of formula -Z—CY—NR$^5$— wherein $R^5$ has the meaning of $R^2$
Y denotes oxygen and sulphur;
X denotes hydrogen and hydroxyl;
Z denotes oxygen or a NH group;
n is a integer of 1 to 4; and
each R independently are the same or different and denote a triiodinated phenyl group, preferably a 2,4,6-triiodinated phenyl group further substituted by two groups $R^4$ wherein each $R^4$ are the same or different and denote a hydrogen atom or a non-ionic hydrophilic moiety, provided that at least one $R^4$ group in the compound of formula (I) is a hydrophilic moiety;
and salts or optical active isomers thereof.

The substituents $R^1$ above are the same or different. Preferably X denotes a hydrogen atom and each $R^1$ then denote the moiety $-(CH_2)_n-R^3-R$. Further it is preferred that each of the $R^3$ groups are the same and denote moiety of formula $-NH-CO-NR^5-$ wherein $R^5$ has the meaning of $R^2$. The $R^1$ moieties will then be of the formula $-(CH_2)_n-NH-CO-NR^5-R$. Even more preferred $R^5$ denotes hydrogen or methyl thus $R^3$ denote the urea residues $-NH-CO-NH-$ and $-NH-CO-N(CH_3)-$ linking the group R to the central alkyl moiety. Hence, in a particularly preferred aspect of the invention n denotes the integer of 1 or 2, and the $R^1$ groups are of the formula $-(CH_2)_{1,2}-NH-CO-NH-R$ or $-(CH_2)_{1,2}-NH-CO-N(CH_3)-R$. Urethane functions of the formula formula $-(CH_2)_{1,2}-O-CO-NH-R$ are also preferred.

It is further preferred that the substituent $R^2$ of the compound of formula (I) denotes a hydrogen atom or a methyl group.

Each of the iodinated R group should be the same or different and preferably denote a 2,4,6-triiodinated phenyl group, further substituted by two groups $R^4$ in the remaining 3 and 5 positions in the phenyl moiety.

The non-ionic hydrophilic moieties may be any of the non-ionizing groups conventionally used to enhance water solubility. Hence, the $R^4$ substituents may be the same or different and shall preferably all denote a non-ionic hydrophilic moiety comprising esters, amides and amine moieties, that optionally are further substituted by a straight chain or branched chain $C_{1-10}$ alkyl groups, preferably $C_{1-5}$ alkyl groups, and optionally additionally with one or more $CH_2$ or CH moieties replaced by oxygen or nitrogen atoms. The $R^4$ substituents may also further contain one or more groups selected from oxo, hydroxyl, amino or carboxyl derivative, and oxo substituted sulphur and phosphorus atoms. Each of the straight or branched alkyl groups are preferably containing 1 to 6 hydroxy groups and more preferably 1 to 3 hydroxy groups. Therefore, in a further preferred aspect, the $R^4$ substituents are the same or different and are polyhydroxy $C_{1-5}$ alkyl, hydroxyalkoxyalkyl with 1 to 5 carbon atoms and hydroxypolyalkoxyalkyl with 1 to 5 carbon atoms, and are attached to the iodinated phenyl group via an amide linkage.

The $R^4$ groups of the formulas listed below are particularly preferred:
—CONH—CH$_2$—CH$_2$OH
—CONH—CH$_2$—CHOH—CH$_2$OH
—CON(CH$_3$)CH$_2$—CHOH—CH$_2$OH
—CONH—CH—(CH$_2$OH)$_2$
—CON—(CH$_2$—CH$_2$OH)$_2$
—CON—(CH$_2$—CH$_2$OH—CH$_2$OH)$_2$
—CONH$_2$
—CONHCH$_3$
—NHCOCH$_2$OH —N(COCH$_3$)H
—N(COCH$_3$)C$_{1-3}$ alkyl
—N(COCH$_3$)— mono, bis or tris-hydroxy C$_{1-4}$ alkyl
—N(COCH$_2$OH)— hydrogen, mono, bis or tris-hydroxy C$_{1-4}$ alkyl
—N(CO—CHOH—CH2OH)— hydrogen, mono, bis or tri-hydroxylated C$_{1-4}$ alkyl.
—N(CO—CHOH—CHOH—CH2OH)— hydrogen, mono, bis or trihydroxylated C$_{1-4}$ alkyl.
—N(COCH$_2$OH)$_2$
—CON(CH$_2$—CHOH—CH$_2$OH)(CH$_2$—CH$_2$OH)
—CONH—C(CH$_2$OH)$_3$ and
—CONH—CH(CH$_2$OH)(CHOH—CH$_2$OH)
-morpholine-4-carbonyl.

Still more preferably the R$^4$ groups will be equal or different and denote one or more moieties of the formulas —CON(CH$_3$)CH$_2$—CHOH—CH$_2$OH, —CONH—CH$_2$—CHOH—CH$_2$OH, —CONH—CH—(CH$_2$OH)$_2$, —CON—(CH$_2$—CH$_2$OH)$_2$, —CON—(CH$_2$—CH$_2$OH—CH$_2$OH)$_2$, —CONH—CH$_2$—CHOH—CH$_2$OH, —NHCOCH$_2$OH and —N(COCH$_2$OH)— mono, bis or tris-hydroxy C$_{1-4}$ alkyl, and even more preferably all R$^4$ groups are equal and denote one of these moieties.

Most preferred all substituents R$^1$ in formula (I) are equal.

In particularly preferred examples the preferred structures according to the invention include the compound of formula (IIa) to (IIg) below. In formula (IIa) the central C(R$^1$)$_3$R$^2$ group of formula (I) wherein R$^1$ denotes the (CX$_2$)$_n$—R$^3$— moiety is a 2-ureamethyl-2-methylpropane-1,3 urea residue and the R groups are the same and are 2,4,6-triiodo-3,5-(2,3-dihydroxypropyl carbamido) phenyl residues.

Formula (IIa)

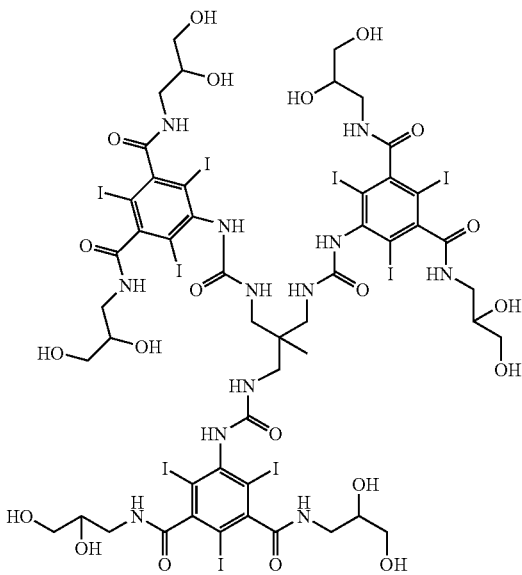

Formula (IIb)

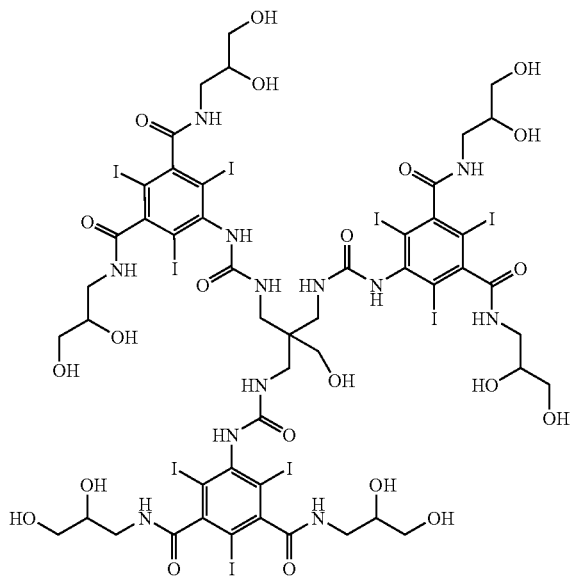

Formula (IIc)

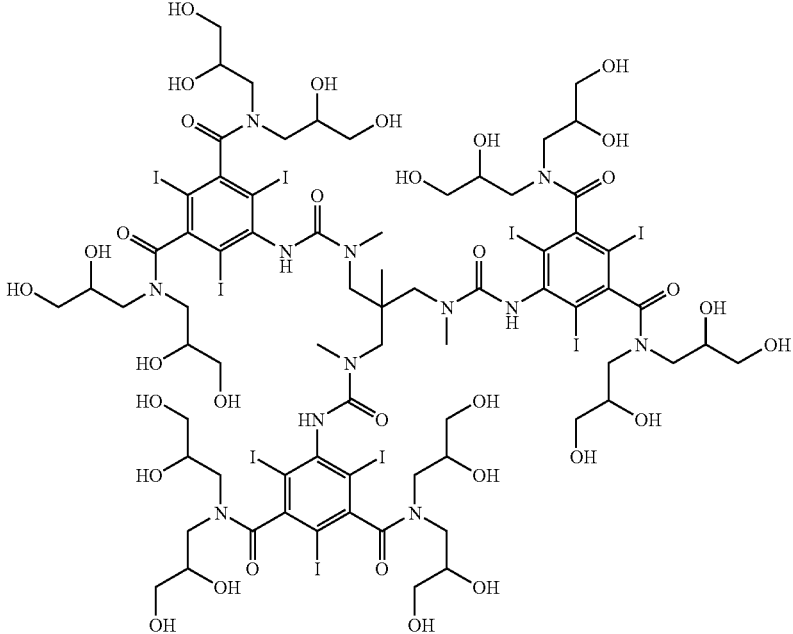

Formula (IId)
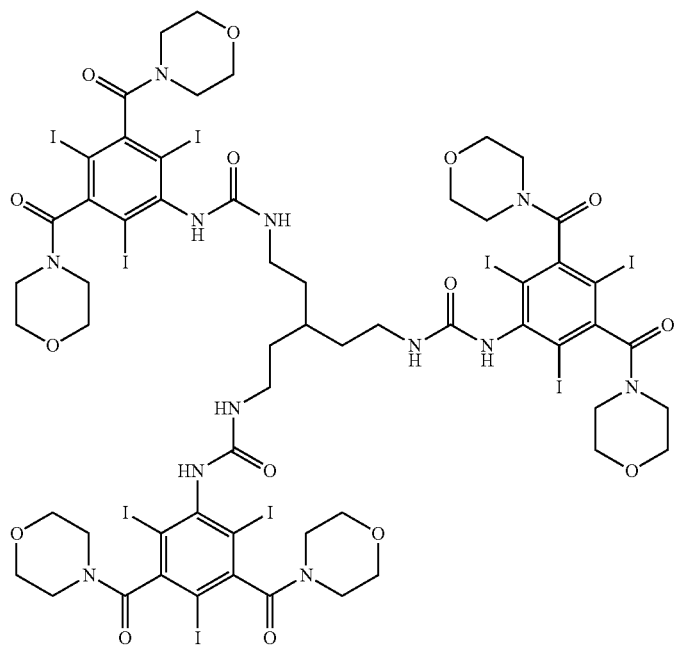
Formula (IIe)
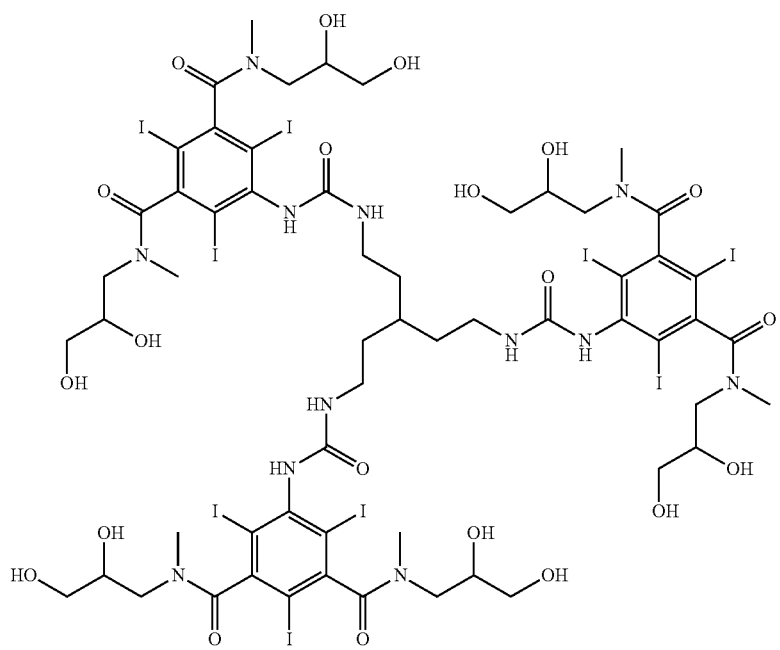

Formula (IIf)
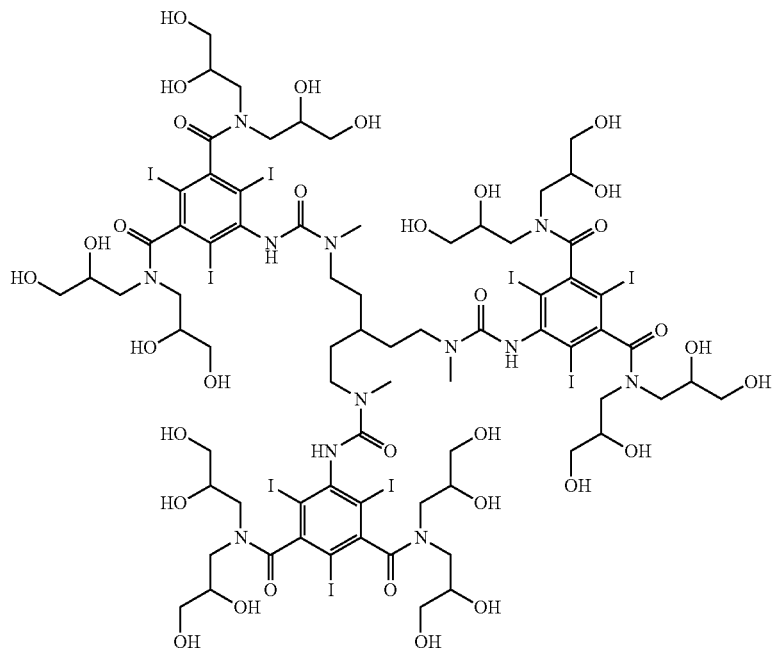
Formula (IIg)
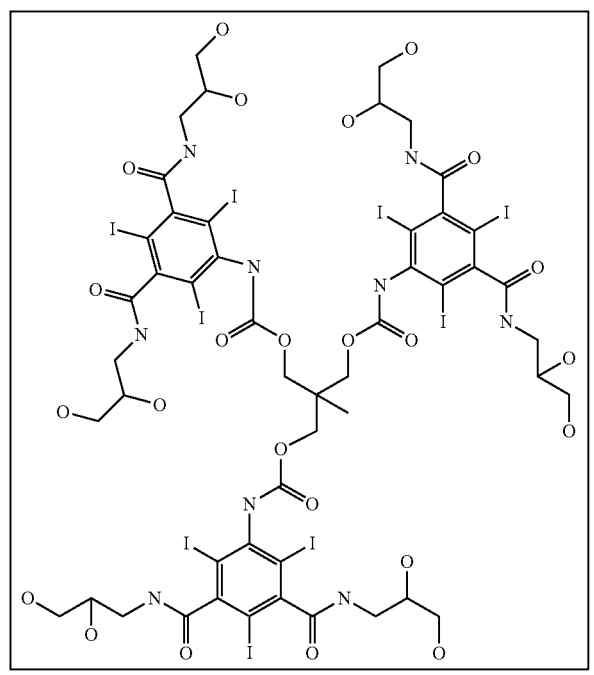

The compounds of formula (I) will attain a star-form with the relatively bulky iodinated phenyl substituents filling up the area between the 3 arms of the star. The molecule will therefore adopt a relatively round or globular form. Globular molecules will usually have enhanced solubility compared with similar molecules with a more planar structure.

At an iodine concentration of 320 mg/ml, which is a common concentration for commercially available iodinated contrast media, the concentration of the compound of formula (I) will be approximately 0.28 M (Molar). The contrast medium will also be hypoosmolar at this iodine concentration, and this is an advantageous property with regards to the nephrotoxicity of the contrast medium. It is also possible to add electrolytes to the contrast medium to lower the cardiovascular effects as explained in WO 90/01194 and WO 91/13636.

Compounds of formula (I) also comprises optical active isomers. Both enantiomerically pure products as well as mixtures of optical isomers are included.

The compounds of the invention may be used as contrast agents and may be formulated with conventional carriers and excipients to produce diagnostic contrast media.

Thus viewed from a further aspect the invention provides a diagnostic composition comprising a compound of formula (I) as described above together with at least one physiologically tolerable carrier or excipient, e.g. in aqueous solution for injection optionally together with added plasma ions or dissolved oxygen.

The contrast agent composition of the invention may be in a ready to use concentration or may be a concentrate form for dilution prior to administration. Generally compositions in a ready to use form will have iodine concentrations of at least 100 mg I/ml, preferably at least 150 mg I/ml, with concentrations of at least 300 mg I/ml, e.g. 320 mg I/ml being preferred. The higher the iodine concentration, the higher is the diagnostic value in the form of X-ray attenuation of the contrast media. However, the higher the iodine concentration the higher is the viscosity and the osmolality of the composition. Normally the maximum iodine concentration for a given contrast media will be determined by the solubility of the contrast enhancing agent, e.g. the iodinated compound, and the tolerable limits for viscosity and osmolality.

For contrast media which are administered by injection or infusion, the desired upper limit for the solution's viscosity at ambient temperature (20° C.) is about 30 mPas, however viscosities of up to 50 to 60 mPas and even more than 60 mPas can be tolerated. For contrast media given by bolus injection, e.g. in angiographic procedures, osmotoxic effects must be considered and preferably the osmolality should be below 1 Osm/kg $H_2O$, preferably below 850 mOsm/kg $H_2O$ and more preferably about 300 mOsm/kg $H_2O$.

With the compounds of the invention such viscosity, osmolality and iodine concentrations targets can be met. Indeed, effective iodine concentrations can be reached with hypotonic solutions. It may thus be desirable to make up the solution's tonicity by the addition of plasma cations so as to reduce the toxicity contribution that derives from the imbalance effects following bolus injection. Such cations will desirably be included in the ranges suggested in WO 90/01194 and WO 91/13636.

In particular, addition of sodium and calcium ions to provide a contrast medium isotonic with blood for all iodine concentrations is desirable and obtainable. The plasma cations may be provided in the form of salts with physiologically tolerable counterions, e.g. chloride, sulphate, phosphate, hydrogen carbonate etc., with plasma anions preferably being used.

The compounds of the general formula (I) can be synthesized by multistep procedures from starting materials that are either known from the state of art or that are commercially available. Tri-iodinated phenyl groups R and precursors thereof are commercially available or can be produced following procedures described or referred to e.g. in WO95/35122 and WO98/52911. 5-amino-2,4,6-triiodo-isophtalic acid for example is available e.g. from Aldrich and 5-amino-2,4,6-triiodo-N,N'-bis(2,3-dihydroxypropyl)-isophtalamide is commercially available e.g. from Fuji Chemical Industries, Ltd. Alkyl-amines are likewise commercially available or readily synthesized from available starting materials.

To synthesize compounds of formula (I), the $R^4$ groups or precursors thereof denoted $R^{4'}$ on the R group are protected and a reactive substituent is formed that is brought to react with an alkyl-triamine. Suitable, the reactive functionality on the R-group can be a group containing an acid chloride function. The $R^{4'}$ precursor groups can be deprotected and/or completed after the trimeric product is formed. The procedure is explained in detail in the following and involves the following steps:

1) The isocyanate is formed by reacting the aniline with phosgene.
2) The compound from 1) is dissolved in dichloromethane (or any other suitable solvent) and added to this is an amine at ambient temperature to form a urea linkage.
3) The compound form 2) is hydrolyzed to yield the final product.

More specific, compounds of formula (I) wherein R denotes a 2,4,6-triiodo-N,N'-bis(2,3-dihydroxypropyl)-isophtalamide residue can be prepared by the following steps: 5-amino-2,4,6-triiodo-N,N'-bis(2,3-dihydroxypropyl)-isophtalamide (15 g, 17 mmol) in 1,4-dioxane (40 mL) was added to about 11 equivalents of a 20% phosgene solution in toluene (100 mL, 200 mmol) at ambient temperature. The solution was heated at about 60° C. for about 15 hours. The reaction was allowed to cool to ambient temperature and then concentrated at reduced pressure to yield an off white, semi-crystalline solid. Dioxane (50 mL×2) was added and removed slowly at reduced pressure to give an off white, semi-crystalline solid which was placed on a vacuum line to remove any residual solvent. $^1H$ and $^{13}C$ NMR confirmed the isocyanate had formed. The newly formed isocyanate was dissolved in dichloromethane and treated with a triamine (about 0.3 equivalents) under a nitrogen atmosphere at ambient temperature for about 18 hours. The desired tris-urea can be isolated by silica gel column chromatography.

The invention will hereinafter be further illustrated with a non-limiting example.

EXAMPLE 1

N,N'-Bis-(2,3-dihydroxy-propyl)-5-[3-(3-{3-[N,N'-bis-(2,3-dihydroxy-propyl)-2,4,6-triiodo-phenyl]-ureido}-2-{3-[N,N'-bis-(2,3-dihydroxy-propyl)-2,4,6-triiodo-phenyl]-ureidomethyl}-2-methyl-propyl)-ureido]-2,4,6-triiodoisophthalamide

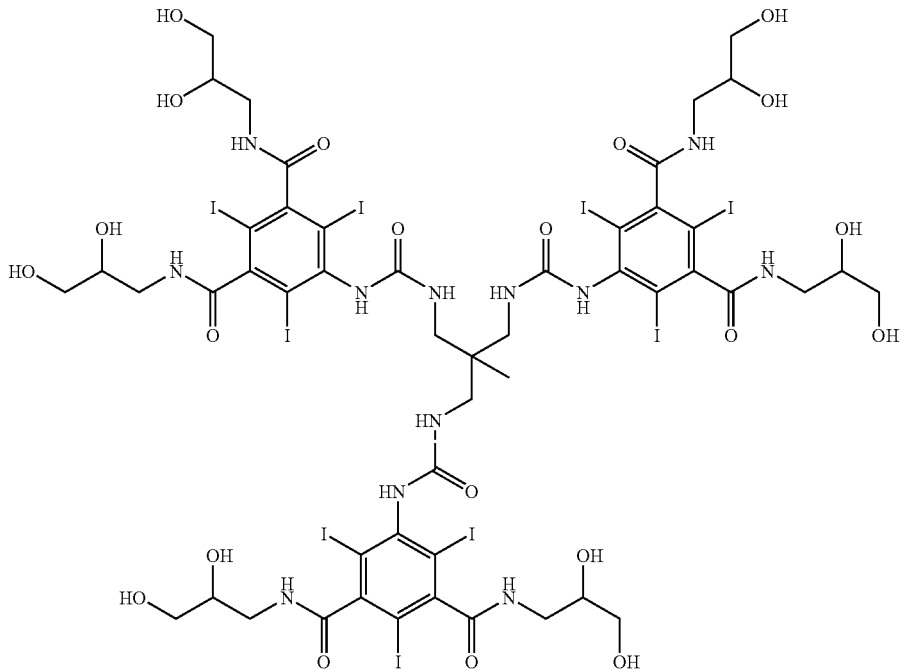

a) Preparation of acetic acid 2-acetoxy-3-[3-(2,3-diacetoxy-propylcarbamoyl)-2,4,6-triodo-5-isocyanato-benzoylamino]-propyl-1-ester To a solution of acetic acid 2-acetoxy-3-[3-amino-5-(2,3-diacetoxy-propylcarbamoyl)-2,4,6-triodo-benzoylamino]-propyl ester (4 mmol) in 1,4 dioxane (20 mL) was added ~11 equivalents of 20% phosgene in toluene (44 mL) at ambient temperature. The flask was sealed and heated to 60° C. for 15 hours. The reaction was cooled to ambient temperature and then concentrated at reduced pressure to yield an off white solid. Dioxane (50 mL ×2) ws added and removed slowly at reduced pressure to give an off-white solid which was placed on a vacuum line to remove any residual solvent. The material was used without further purification.

$^1$H NMR (CDCl$_3$): 7.43 (m, br, 2H), 5.28 (s, br, 2H), 4.50-4.38 (m, br, 2H), 4.30-4.19 (m, br, 2H), 3.82-3.48 (m, vbr, 4H), 2.05 (s, 12H)

$^{13}$C NMR (CDCl$_3$): 170.7, 170.3, 169.7, 149.8, 123.7, 92.2, 70.0, 63.3, 39.9, 21.3, 20.7.

b) Preparation of Tris-urea from acetic acid 2-acetoxy-3-[3-(2,3-diacetoxy-Propylcarbamoyl)-2,4,6-triodo-5-isocyanato-benzoylamino]-propyl-1-ester To a solution of acetic acid 2-acetoxy-3-[3-(2,3-diacetoxy-propylcarbamoyl)-2,4,6-triodo-5-isocyanato-benzoylamino]-propyl-1-ester (4 g, 4.4×10$^{-3}$ mol) in DCM (80 mL) was added 2-aminomethyl-2-methylpropane-1,3-diamine (170 mg, 1.4×10$^{-3}$ mol) at ambient temperature under a nitrogen atmosphere. After 18 hours the mixture was purified by silica gel chromatography to yield a white crystalline solid (1 g, 25%)

MS (ES$^+$, m/z): 1406 ([M+2H]$^{2+}$, 100%)

c) N,N'-Bis-(2,3-dihydroxy-propyl)-5-[3-(3-{3-[N,N'-bis-(2,3-dihydroxy-propyl)-2,4,6-triiodo-phenyl]-ureido}-2-{3-[N,N'-bis-(2,3-dihydroxy-propyl)-2,4,6-triiodo-phenyl]-ureidomethyl}-2-methyl-propyl)-ureido]-2,4,6-triiodoisophthalamide To a solution of the urea formed from acetic acid 2-acetoxy-3-[3-(2,3-diacetoxy-propylcarbamoyl)-2,4,6-triodo-5-isocyanato-benzoylamino]-propyl-1-ester (1 g, 3.5×10$^{-4}$ mol) in methanol (5 mL) was added sodium methoxide (10 mg, 1.85×10$^{-4}$ mol) under a nitrogen atmosphere at ambient temperature. The mixture was stirred for 18 hours and a white precipitate had formed. This was collected by filtration, washed with methanol and dried at reduced pressure. The material was further purified by HPLC. The yield before HPLC was ~quantitative.

$^{13}$C NMR (DMSO-d$_6$): 170.1, 155.8, 150.1, 144.1, 101.4, 100.9, 89.6, 70.5, 64.4, 43.1, 42.2, 19.3.

MS (ES$^+$, m/z) 2311 ([M+H]$^+$, 40%), 1156 ([M+2H]$^{2+}$, 100%)

EXAMPLE 2

N,N'-Bis-(2,3-dihydroxy-propyl)-5-(3-{3-{3-[3,5-bis-(2,3-dihydroxy-propylcarbamoyl)-2,4,6-triiodo-phenyl]-ureido}-2-hydroxymethyl-2-[3,5-bis-(2,3-dihydroxy-propylcarbamoyl)-2,4,6-triiodo-phenyl]-ureido)-methyl]propyl}-ureido)-2,4,6-triiodo-isophthalamide a) Acetic acid 1-acetoxymethyl-2-[3-(2,3-diacetoxy-propylcarbamoyl)-2,4,6-triiodo-5-isocyanato-benzoylamino]-ethyl ester

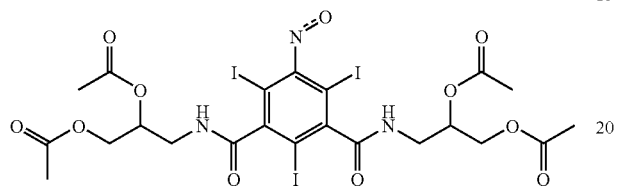

To a solution of acetic acid 1-acetoxymethyl-2-[3-amino-5-(2,3-diacetoxy-propylcarbamoyl)-2,4,6-triiodo-benzoylamino]-ethyl ester (4 mmol) in 1,4-dioxane (20 mL) was added ~11 equivalents of 20% phosgene solution in toluene (44 mL) at ambient temperature. The flask was sealed and the solution was heated at 60° C. for 15 hours. The reaction was allowed to cool to ambient temperature and then concentrated at reduced pressure to yield an off white, semi-crystalline solid. Dioxane (50 mL×2) was added and removed slowly at reduced pressure to give an off white, semi-crystalline solid. The material was used without further purification.

b) Acetic acid 2-acetoxy-3-[3-(3-{3-{3-[3,5-bis-(2,3-diacetoxy-propylcarbamoyl)-2,4,6-triiodo-phenyl]-ureido}-2-hydroxymethyl-2-[(3-[3,5-bis-(2,3-diacetoxy-propylcarbamoyl)-2,4,6-triiodo-phenyl-ureido)-methyl]-propyl}-ureido)-5-(2,3-diacetoxy-propylcarbamoyl)-2,4,6-triiodo-benzoylamino]-propyl ester

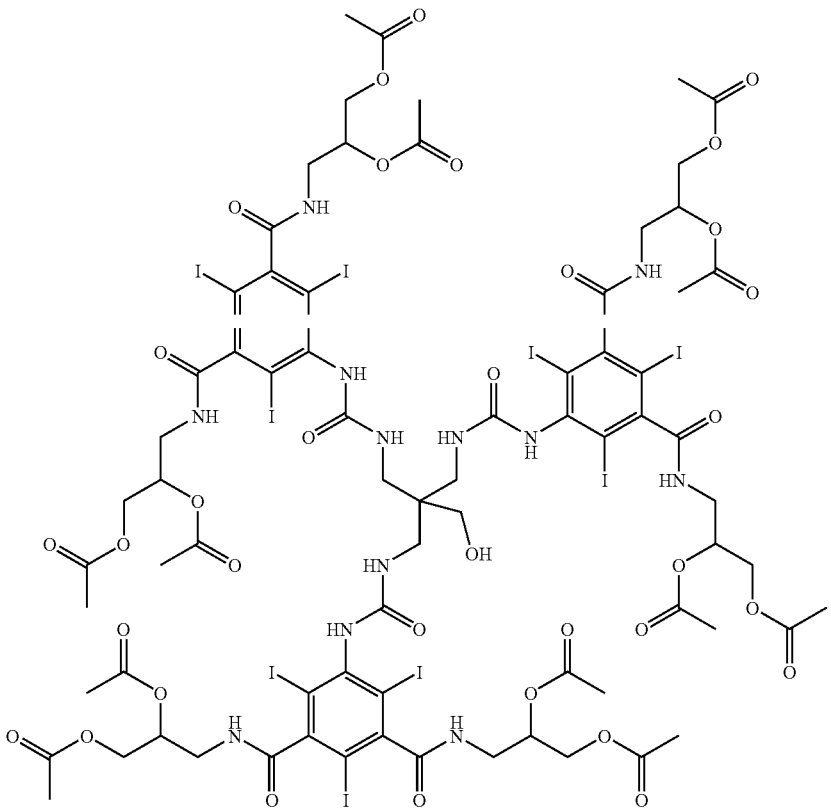

To a solution of acetic acid 1-acetoxymethyl-2-[3-(2,3-diacetoxy-propylcarbamoyl)-2,4,6-triiodo-5-isocyanato-benzoylamino]-ethyl ester (5 g, 5.6 mmol) in DCM was added 3-amino-2,2-bis-aminomethyl-propan-1-ol (240 mgs, 1.8 mmol), the mixture was stirred at ambient temp for 18 hours. The mixture was absorbed onto silica gel and purified via silica gel column eluting with MeOH and DCM. The relevant fractions were concentrated and analysed by LCMS.

MS (ES+) m/2: 1416.04[M/2+H]

c) N,N'-Bis-(2,3-dihydroxy-propyl)-5-(3-{3-{3-[3,5-bis-(2,3-dihydroxy-propylcarbamoyl)-2,4,6-triiodo-phenyl]-ureido}-2-hydroxymethyl-2-[3,5-bis-(2,3-dihydroxy-propylcarbamoyl)-2,4,6-triiodo-phenyl]-ureido)-methyl]propyl}-ureido)-2,4,6-triiodo-isophthalamide

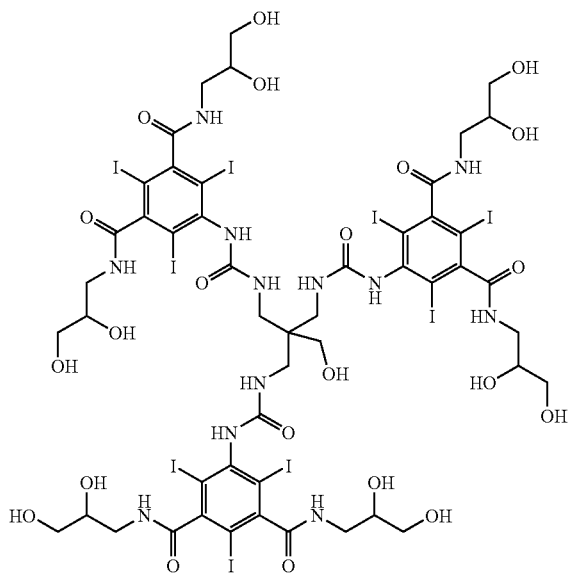

To a solution of acetic acid 2-acetoxy-3-[3-(3-{3-{3-[3,5-bis-(2,3-diacetoxy-propylcarbamoyl)-2,4,6-triiodo-phenyl]-ureido}-2-hydroxymethyl-2-[(3-[3,5-bis-(2,3-diacetoxy-propylcarbamoyl)-2,4,6-triiodo-phenyl-ureido)-methyl]-propyl}-ureido)-5-(2,3-diacetoxy-propylcarbamoyl)-2,4,6-triiodo-benzoylamino]-propyl ester (300 mgs) in methanol was added sodium methoxide (5 mg) at ambient temperature. The mixture was stirred for two hours. To the methanolic solution was added water (10 mL). The solvent was removed at reduced pressure. The residue was purified by preparative HPLC.

MS (ES+) m/2: 1164.02 [M/2+H]

EXAMPLE 3

Tris(N,N,N',N'-Tetrakis-(2,3-dihydroxy-propyl)-5-(3,3-dimethyl-ureido)-2,4,6-triiodo-isophthalamide)ethane a) N,N,N',N'-Tetraallyl-2,4,6-triiodo-5-isocyanato-isophthalamide

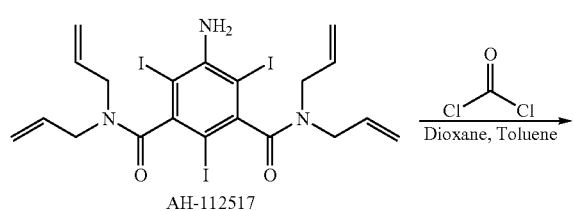

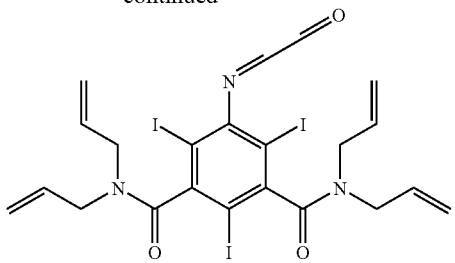

To a solution of N,N,N',N'-tetraallyl-5-amino-2,4,6-triiodo-isophthalamide (5 g, 7 mmol) in 1,4-dioxane (10 mL) was added ~11 equivalents of 20% phosgene solution in toluene (35 mL, 70 mmol) at ambient temperature. The flask was sealed and the solution was heated at 60° C. for 15 hours. The reaction was allowed to cool to ambient temperature and then concentrated at reduced pressure to yield an off white, semi-crystalline solid. Dioxane (50 mL×2) was added and removed slowly at reduced pressure to give an off white, semi-crystalline solid which was placed on a vacuum line to remove any residual solvent. The material was used without further purification.

b) Tris(N,N,N',N'-Tetraallyl-5-(3,3-dimethyl-ureido)-2,4,6-triiodo-isophthalamide)ethane

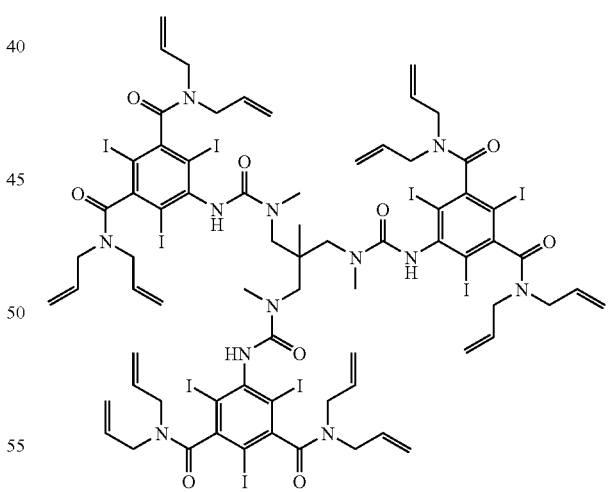

To a solution of N,N,N',N'-tetraallyl-2,4,6-triiodo-5-isocyanato-isophthalamide (5 g, 6.7 mmol) in DCM (20 mL) was added 2,N,N'-trimethyl-2-methylaminomethyl-propane-1,3-diamine (334 mg, 2.1 mmol). The mixture was stirred at ambient temperature for 18 hours. The crude material was separated using silica gel chromatography eluting with methanol/DCM (5-20% methanol). This yielded 900 mgs of the desired trimer.

MS (ES+) m/2: 1195.13[M/2+H]

c) Tris(N,N,N',N'-Tetrakis-(2,3-dihydroxy-propyl)-5-(3,3-dimethyl-ureido)-2,4,6-triiodo-isophthalamide)ethane

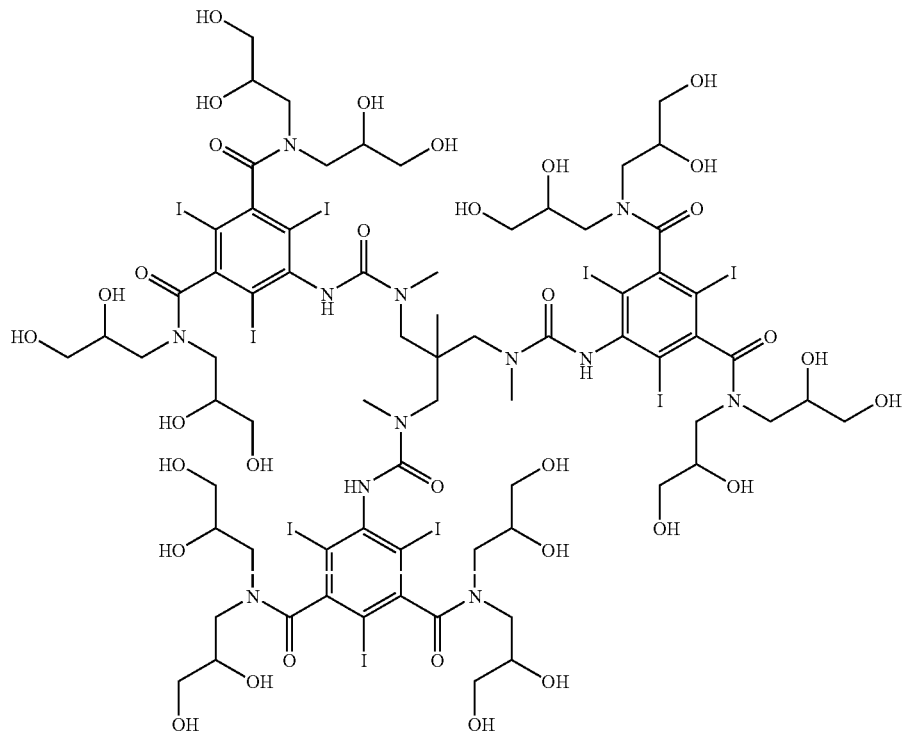

To a solution of tris(N,N,N',N'-Tetraallyl-5-(3,3-dimethyl-ureido)-2,4,6-triiodo-isophthalamide)ethane (900 mg, 0.38 mmol) in acetone/water (9:1) was added N-methylmorpholine N-oxide (1.06 g, 9 mmol) and a 1% solution of osmium tetroxide. The orange solution was stirred at ambient temperature. After stirring for 24 hours the mixture was concentrated to yield a gum. The crude material was separated using preparative HPLC. This yielded 800 mgs of the desired trimer.
MS (ES+) m/2: 1400.59 [M/2+H]

EXAMPLE 4

Tris-(ethyl-3-[2,4,6-triiodo-3,5-bis-(morpholine-4-carbonyl)-phenyl]-urea)methane a) [3-Amino-2,4,6-triiodo-5-(morpholine-4-carbonyl)-phenyl]-morpholin-4-yl-methanone

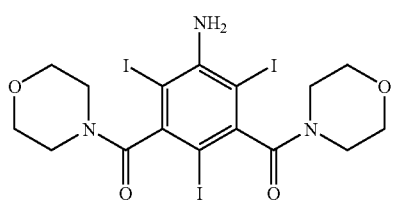

The 5-amino-2,4,6-triiodo-isophthaloyl dichloride (50 g, 84 mmol) was dissolved in anhydrous THF (200 ml), morpholine (29 ml, 333 mmol) was dissolved in 50 ml THF, and added dropwise to the solution over 1 hour. The mixture stirred overnight at ambient temperature. The crude product was loaded onto silica gel (100 g) and separated using a 750 g column eluting with DCM/EtOAc (1:1). This yielded 9 g of the [3-amino-2,4,6-triiodo-5-(morpholine-4-carbonyl)-phenyl]-morpholin-4-yl-methanone.
1H NMR (300 MHz, CDCl$_3$) ☐ 3.20 (m, 4H), 3.75 (m, vbr, 12 H), 5.09 (s, br, 2H)
MS (ES+) m/z: 698.79 [M+H]

b) Morpholin-4-yl-[2,4,6-triiodo-3-isocyanato-5-(morpholine-4-carbonyl)-phenyl]-methanone

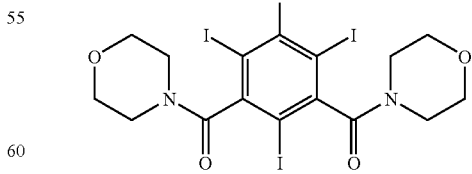

To a solution of [3-Amino-2,4,6-triiodo-5-(morpholine-4-carbonyl)-phenyl]-morpholin-4-yl-methanone (8 g, 11.4 mmol) in 1,4-dioxane (40 mL) was added ~11 equivalents of 20% phosgene solution in toluene (60 mL, 120 mmol) at ambient temperature, the solution was heated at 50° C. for 15 hours. The reaction was allowed to cool to ambient temperature and then concentrated at reduced pressure to yield an off white, semi-crystalline solid. Dioxane (30 mL×2) was added and removed slowly at reduced pressure to give a light brown, semi-crystalline solid which was placed on a vacuum line to remove any residual solvent. The material was used without further purification.

c) Tris-(ethyl-3-[2,4,6-triiodo-3,5-bis-(morpholine-4-carbonyl)-phenyl]-urea)methane

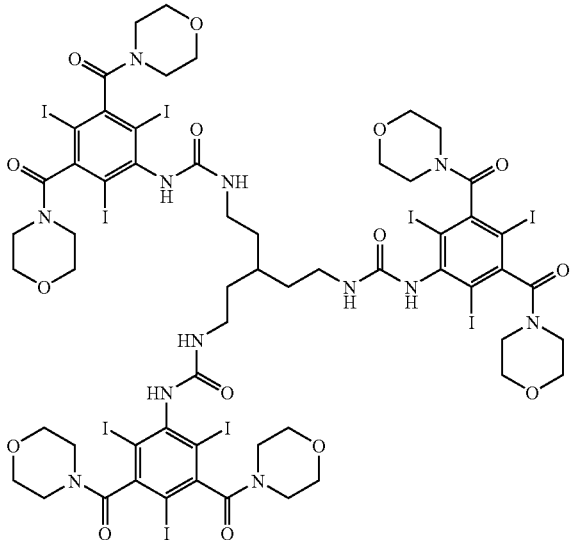

To a solution of morpholin-4-yl-[2,4,6-triiodo-3-isocyanato-5-(morpholine-4-carbonyl)-phenyl]-methanone (4 g, 5.5 mmol) in DCM was added 3-(2-Amino-ethyl)-pentane-1,5-diamine (266 mgs, 1.83 mmol), the mixture was stirred at ambient temp for 18 hours. The reaction mixture was separated by preparative HPLC. This yielded 250 mg of the desired material.

MS (ES+) m/2: 1158.37 [M/2+H]

EXAMPLE 5

Tris-(N,N'-bis-(2,3-dihydroxy-propyl)-5-(3-ethyl-ureido)-2,4,6-triiodo-N,N'-dimethyl-isophthalamide)methane a) N,N'-Diallyl-5-amino-2,4,6-triiodo-N,N'-dimethyl-isophthalamide

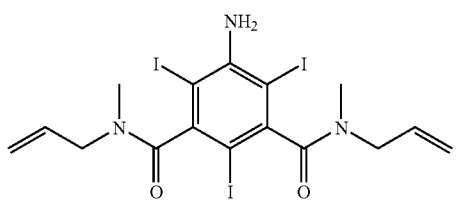

5-Amino-2,4,6-triiodo-isophthaloyl dichloride (38 g, (64 mmol) is dissolved in anhydrous THF (200 ml), the N-diallylamine (25 ml, 270 mmol) was dissolved in 50 ml THF, and added dropwise to the solution over 1 hour. The mixture stirred overnight at ambient temperature. TLC analysis (EtOAc/Petrol (1:1)) gave one spot at ~0.30 Rf. The material was purified by silica gel chromatography.

1H NMR (300 MHz, CDCl$_3$) □ 2.75 (s, 3H), 3.25 (s, 3H), 3.71 (m, 2H), 4.15 (m, 2H), 5.32 (m, br, 4H), 5.92 (m, br, 2H)

MS (ES+) m/z: 666.80 [M+H]

b) N,N'-Diallyl-2,4,6-triiodo-5-isocyanato-N,N'-dimethyl-isophthalamide

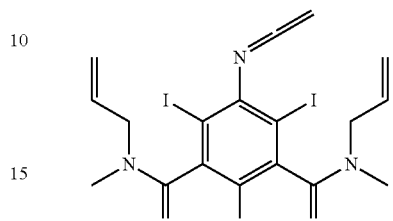

To a solution of N,N'-diallyl-5-amino-2,4,6-triiodo-N,N'-dimethyl-isophthalamide (5 g, 7.5 mmol) in 1,4-dioxane (10 mL) was added ~11 equivalents of 20% phosgene solution in toluene (35 mL, 70 mmol) at ambient temperature, the solution was heated at 60° C. for 15 hours. The reaction was allowed to cool to ambient temperature and then concentrated at reduced pressure to yield an off white, semi-crystalline solid. Dioxane (50 mL×2) was added and removed slowly at reduced pressure to give an off white, semi-crystalline solid which was placed on a vacuum line to remove any residual solvent. The material was used without further purification.

c) Tris(N,N'-Diallyl-5-(3-ethyl-ureido)-2,4,6-triiodo-N,N'-dimethyl-isophthalamide)methane

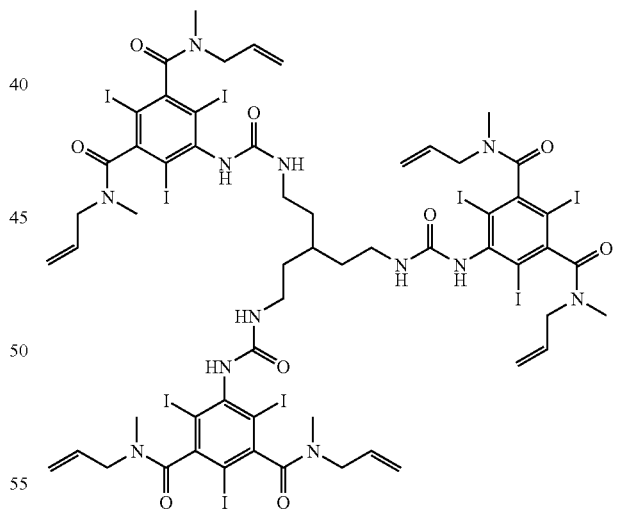

To a solution of N,N'-diallyl-2,4,6-triiodo-5-isocyanato-N,N'-dimethyl-isophthalamide (5 g, 7.2 mmol) in DCM was added 3-(2-amino-ethyl)-pentane-1,5-diamine (348 mgs, 2.4 mmol), the mixture was stirred at ambient temp for 18 hours. The mixture was absorbed onto silica gel and purified using a companion and a 120 g silica gel column eluting with MeOH and DCM (5-25% methanol). This yielded 1.7 g of solid which was found to be the desired material.

MS (ES+) m/2: 1111.31 [M/2+H]

d) Tris-(N,N'-bis-(2,3-dihydroxy-propyl)-5-(3-ethyl-ureido)-2,4,6-triiodo-N,N'-dimethyl-isophthalamide)methane

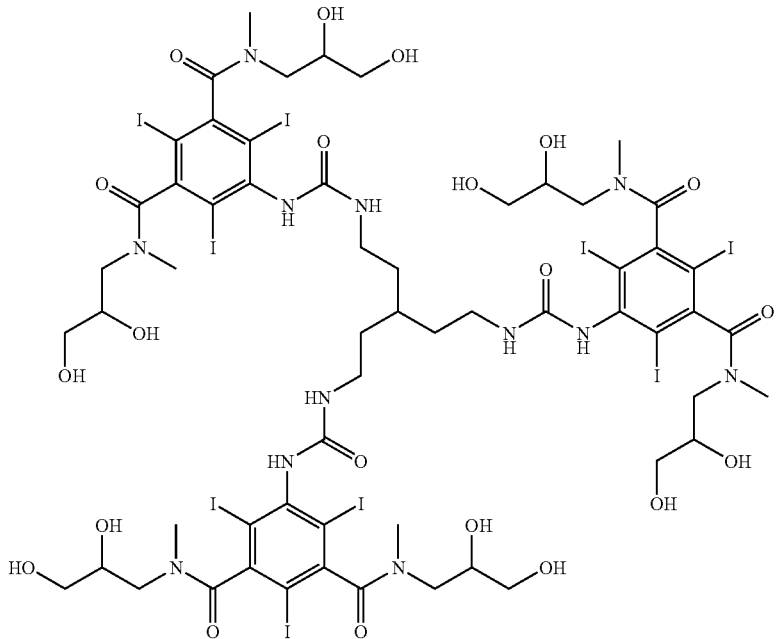

To a solution of tris(N,N'-Diallyl-5-(3-ethyl-ureido)-2,4,6-triiodo-N,N'-dimethyl-isophthalamide)methane (1.70 g, 0.77 mmol) in acetone/water (9:1) was added N-methylmorpholine N-oxide (1.10 g, 9 mmol) and a 1% solution of osmium tetroxide. The solution was stirred at ambient temperature. After stirring for 24 hours the mixture was concentrated to yield a gum. The crude material was separated using preparative HPLC. This yielded 350 mgs of the titled compound.
MS (ES+) m/2: 1211.72 [M/2+H]

EXAMPLE 6

Tris(N,N,N',N'-Tetrakis-(2,3-dihydroxy-propyl)-2,4,6-triiodo-5-(3-methyl-3-Propyl-ureido)-isophthalamide)methane a) Tris(N,N,N',N'-tetraallyl-5-(3-ethyl-ureido)-2,4,6-triiodo-isophthalamide)methane

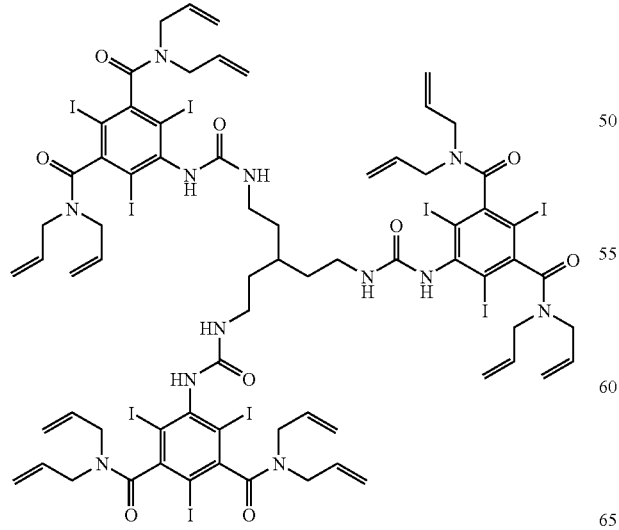

Molecular Weight = 2374.62

To a solution of N,N,N',N'-tetraallyl-2,4,6-triiodo-5-isocyanato-isophthalamide (5 g, 6.9 mmol) in DMF was added 3-(2-amino-ethyl)-pentane-1,5-diamine (331 mgs, 2.3 mmol), the mixture was stirred at ambient temp for 18 hours. The mixture was washed with water (2×100 mL) and the organics were dried and concentrated. The residue was dissolved in DCM (10 mL) and loaded on to a 120 g silica gel column. The mixture was separated by eluting with DCM/MeOH (5 to 25% methanol). The desired trimer was isolated in a yield of 1.25 g (24%).

MS (ES+) m/2: 1187.82 [M/2+H]

b) Tris(N,N,N',N'-Tetrakis-(2,3-dihydroxy-propyl)-2,4,6-triiodo-5-(3-methyl-3-propyl-ureido)-isophthalamide)methane

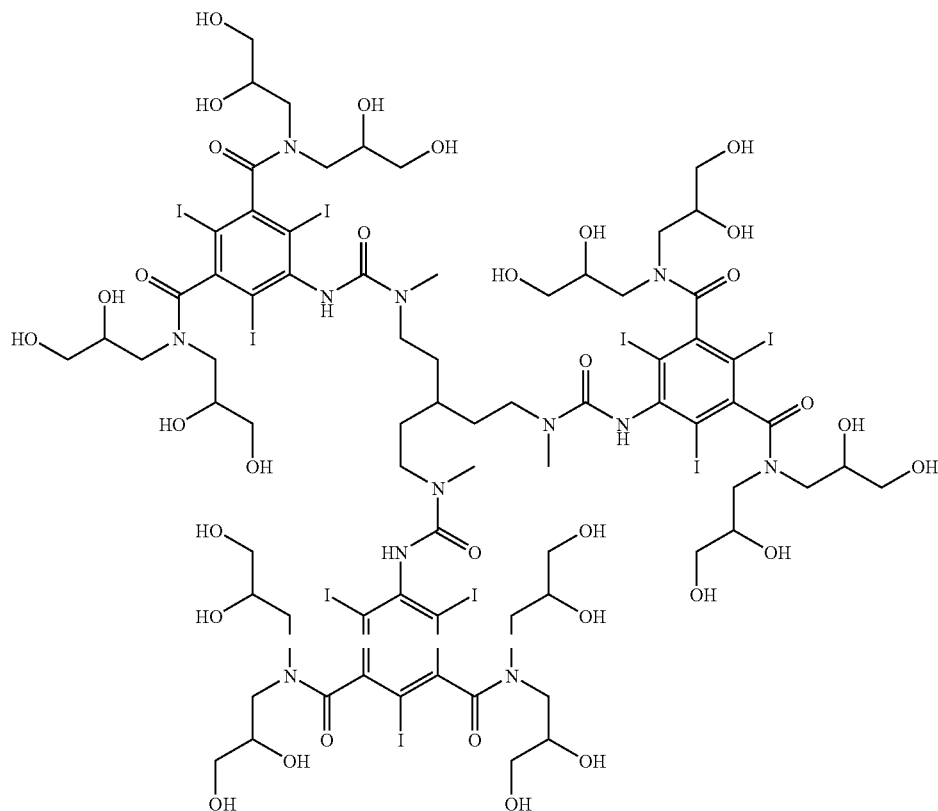

To a solution of tris(N,N,N',N'-tetraallyl-5-(3-ethyl-ureido)-2,4,6-triiodo-isophthalamide)methane (1.25 g, 0.53 mmol) in acetone/water (9:1) was added N-methylmorpholine N-oxide (1.43 g, 12 mmol) and a 1% solution of osmium tetroxide. The solution was stirred at ambient temperature. After stirring for 24 hours the mixture was concentrated to yield a gum. The crude material was separated using preparative HPLC. This yielded 350 mgs of the desired trimer.

MS (ES+) m/2: 1391.9 [M/2+H]

EXAMPLE 7

Tris-{3-[3,5-bis-(2,3-dihydroxypropylcarbamoyl)-2,4,6-triiodo-phenylcarbamoyloxy-propyl}methane a) Tris-{3-[3,5-bis-(2,3-diacetoxypropylcarbamoyl)-2,4,6-triiodo-phenylcarbamoyloxy-propyl}methane

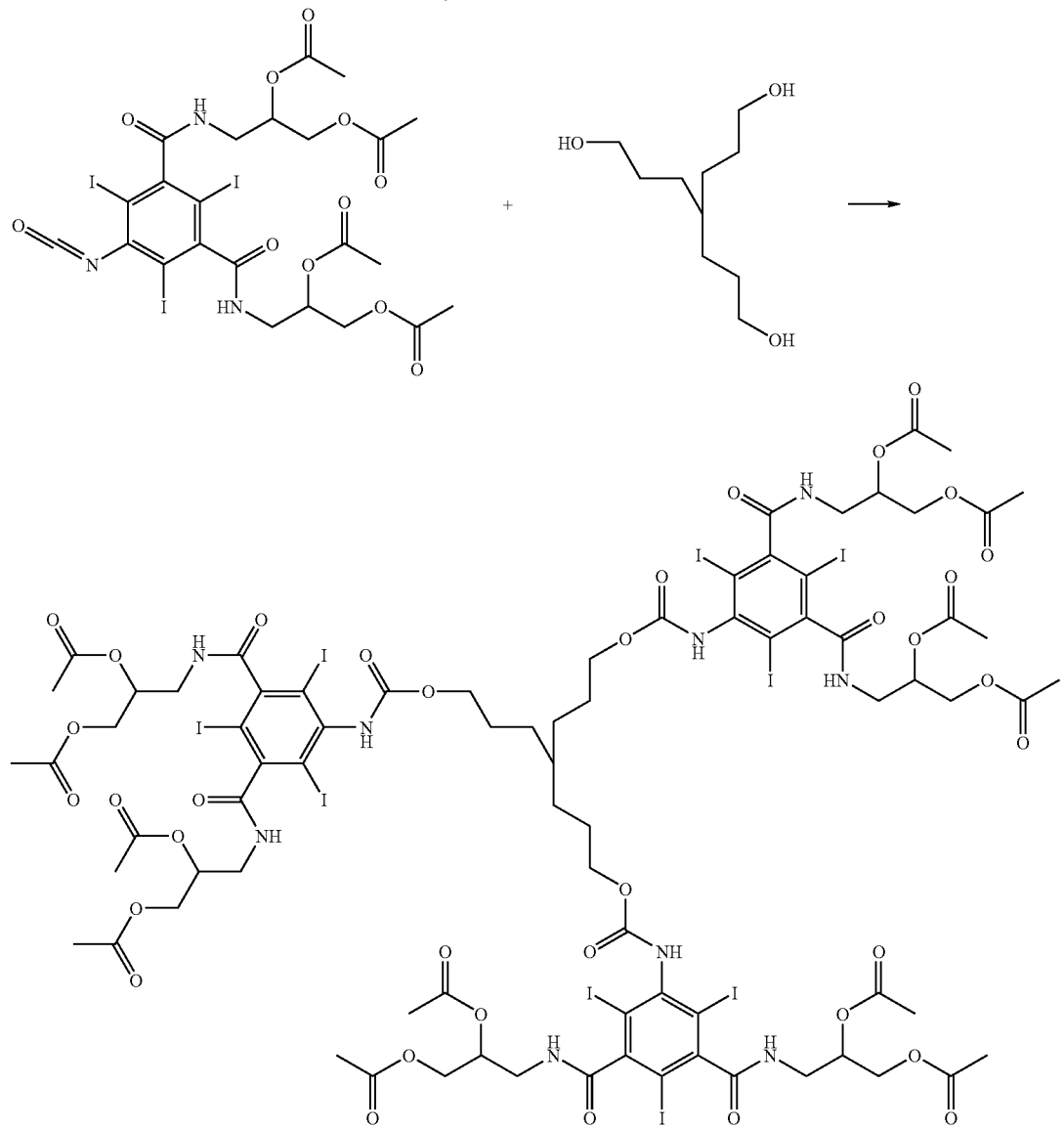

Acetic acid 1-acetoxymethyl-2-[3-amino-5-(2,3-diacetoxy-propylcarbamoyl)-2,4,6-triiodo-benzoylamino]-ethyl ester (8.99 g, 1 mmol) is dissolved in anhydrous DMF (20 ml) and tris(3-hydroxypropyl)methane (0.63 g, 0.33 mmol) is added. After 18 h the solvent is evaporated and the product isolated by chromatography on silica gel.

b) Tris-{3-[3,5-bis-(2,3-dihydroxypropylcarbamoyl)-2,4,6-triiodo-phenylcarbamoyloxy-propyl}methane To a solution of tris-{3-[3,5-bis-(2,3-diacetoxypropylcarbamoyl)-2,4,6-triiodo-phenylcarbamoyloxy-propyl}methane (1.0 g) in methanol (15 ml) is added 32% aqueous ammonia (2 ml) and the mixture stirred for 18 h. The crude product is purified by preparative HPLC.

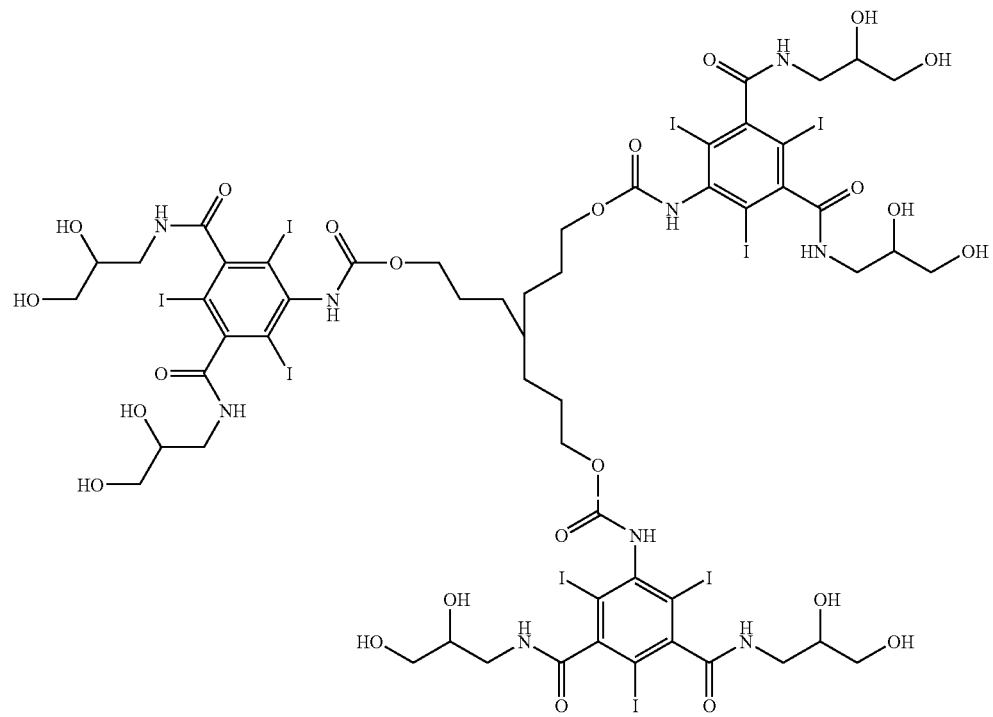
EXAMPLE 8
Tris([3,5-Bis-(2,3-dihydroxy-propylcarbamoyl)-2,4,6-triiodo-phenyl]-carbamic acid methyl ester)ethane
a) Tris(Acetic acid 2-acetoxy-3-[3-(2,3-diacetoxy-propylcarbamoyl)-2,4,6-triiodo-5-methoxycarbonylamino-benzoylamino]-propyl ester)ethane
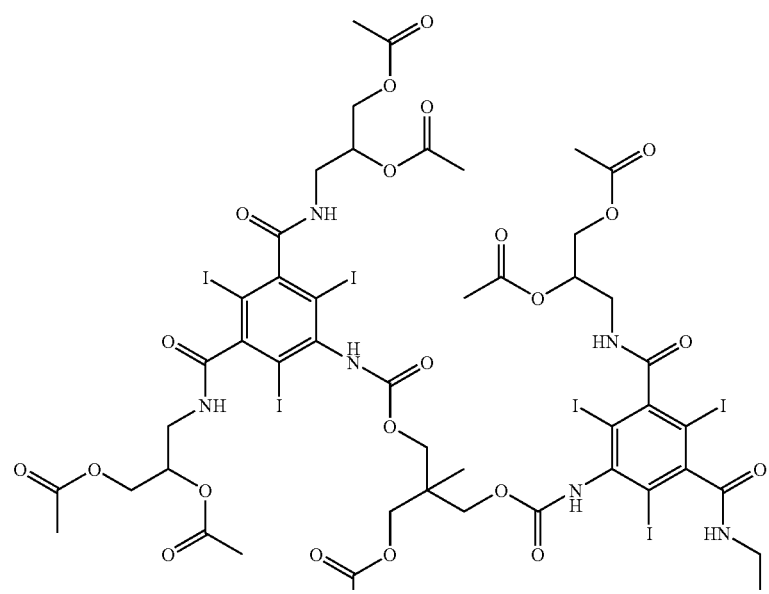

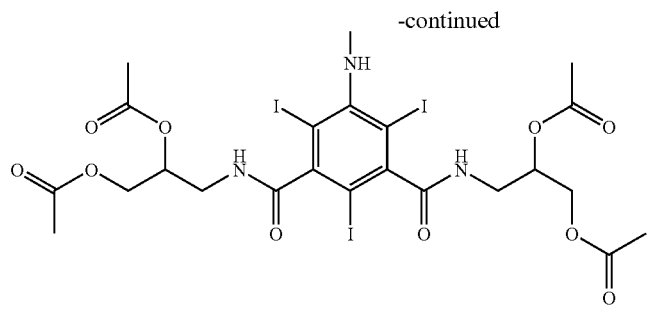
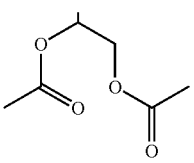

To a solution of acetic acid 1-acetoxymethyl-2-[3-(2,3-diacetoxy-propylcarbamoyl)-2,4,6-triiodo-5-isocyanato-benzoylamino]-ethyl ester (~5 g, 5.6 mmol) in DCM (20 mL) under a nitrogen atmosphere was added 2-hydroxymethyl-2-methyl-propane-1,3-diol (216 mg, 1.8 mmol). The mixture was stirred at ambient temperature for 18 hours. The solvent was removed at reduced pressure; the white solid was dissolved in methanol and adsorbed onto silica gel. The crude mixture was separated on a 120 g silica gel column eluting with methanol in DCM. This yielded the titled compound in a 19% yield.

LCMS (ES+): 1409.62 [M/2+H]

b) Tris([3,5-Bis-(2,3-dihydroxy-propylcarbamoyl)-2,4,6-triiodo-phenyl]-carbamic acid methyl ester) ethane

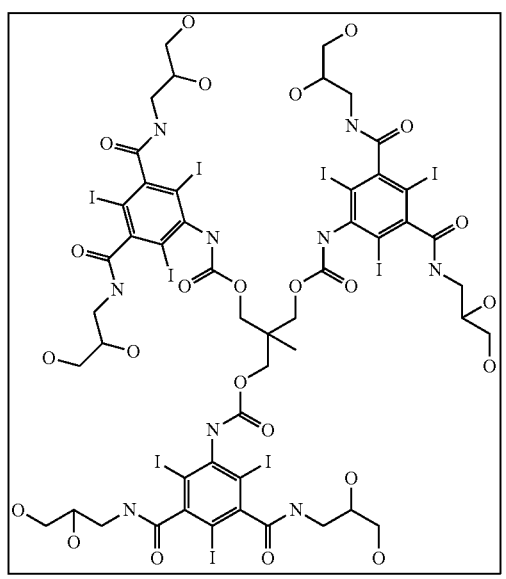

To a solution of tris(acetic acid 2-acetoxy-3-[3-(2,3-diacetoxy-propylcarbamoyl)-2,4,6-triiodo-5-methoxycarbonylamino-benzoylamino]-propyl ester)ethane (1 g, 0.35 mmol) in methanol was added sodium methoxide (10 mg) at ambient temperature under a nitrogen atmosphere. The mixture was stirred for 2 hours. To the methanolic solution was added water, the methanol was removed at reduced pressure. The aqueous layer was cooled until frozen and then the material was freeze dried. This yielded 800 mgs of a white solid.

LCMS (ES+): 1157.07 [M/2+H]

The invention claimed is:

1. A compounds of formula (I)

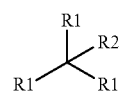

Formula (I)

and salts or optical active isomers thereof
wherein
each $R^1$ are the same or different and denote a moiety —$(CX_2)_n$—$R^3$—R;
$R^2$ denotes hydrogen or $C_1$-$C_4$ alkyl where the alkyl group may be substituted by hydroxyl groups or interrupted by an oxygen atom;
each $R^3$ are the same or different and denote a moiety of formula —Z—CY—NR$^5$—
wherein $R^5$ has the meaning of $R^2$
Y denotes oxygen or sulphur;
X denotes hydrogen or hydroxyl;
Z denotes oxygen or a NH group;
n is a integer of 1 to 4; and
each R independently are the same or different and denote a triiodinated phenyl group, further substituted by two groups $R^4$ wherein each $R^4$ are the same or different and denote a hydrogen atom or a non-ionic hydrophilic moiety comprising esters, amides or amine moieties, provided that at least one $R^4$ group in the compound of formula (I) is a hydrophilic moiety.

2. The compound as claimed in claim 1 wherein each $R^1$ are the same or different and denote a moiety $(CH_2)_n$—$R^3$—R where $R^3$, R and n are as defined in claim 1.

3. The compound as claimed in claim 2 wherein each $R^3$ are the same and denote moiety of formula —NH—CO—NR$^5$— wherein $R^5$ has the meaning of $R^2$.

4. The compound as claimed in claim 3 wherein each $R^3$ denote moiety of formula —NH—CO—NH—.

5. The compound as claimed in claim 3 wherein each $R^3$ denote moiety of formula —NH—CO—N(CH$_3$)—.

6. The compound as claimed in claim 2 wherein each $R^3$ denote moiety of formula —O—CO—NH—.

7. The compound as claimed in claim 1 wherein n denotes the integer of 1 or 2.

8. The compound as claimed in claim 1 wherein $R^2$ denotes hydrogen or methyl.

9. The compound as claimed in claim 1 wherein each R are the same or different and denote a 2,4,6 triiodinated phenyl group, further substituted by two groups $R^4$.

10. The compound as claimed in claim 1 wherein each $R^4$ are the same or different and denote a non-ionic hydrophilic moiety comprising esters, amides or amine moieties, optionally further substituted by a straight chain or branched chain $C_{1-10}$ alkyl groups, optionally with one or more $CH_2$ or CH moieties replaced by oxygen or nitrogen atoms and optionally substituted by one or more groups selected from oxo, hydroxyl, amino or carboxyl derivative, and oxo substituted sulphur and phosphorus atoms.

11. The compound as claimed in claim 10 wherein $R^4$ are the same or different and denote a non-ionic hydrophilic moiety comprising esters, amides or amine moieties, optionally further substituted by a straight chain or branched chain $C_{1-5}$ alkyl groups, optionally with one or more $CH_2$ or CH moieties replaced by oxygen or nitrogen atoms and optionally substituted by one or more groups selected from oxo, hydroxyl, amino or carboxyl derivative, and oxo substituted sulphur and phosphorus atoms.

12. The compound as claimed in claim 11 wherein $R^4$ are the same or different and denote a non-ionic hydrophilic moiety comprising esters, amides or amine moieties, further substituted by a straight chain or branched chain $C_{1-5}$ alkyl groups substituted by 1 to 3 hydroxy groups.

13. The compound as claimed in claim 12 wherein each $R^4$ are the same or different and are polyhydroxy $C_{1-5}$ alkyl, hydroxyalkoxyalkyl with 1 to 5 carbon atoms or hydroxypolyalkoxyalkyl with 1 to 5 carbon atoms attached to the iodinated phenyl group via an amide linkage.

14. The compound as claimed in claim 13 wherein each $R^4$ are the same or different and are selected from groups of the formulas —CONH—CH₂—CH₂OH
—CONH—CH₂—CHOH—CH₂OH
—CON(CH₃)CH₂—CHOH—CH₂OH
—CONH—CH—(CH₂OH)₂
—CON—(CH₂—CH₂OH)₂
—CON—(CH₂—CH₂OH—CH₂OH)₂
—CONH₂
—CONHCH₃
—NHCOCH₂OH
—N(COCH₃)H
—N(COCH₃) $C_{1-3}$ alkyl
—N(COCH₃)— mono, bis or tris-hydroxy $C_{1-4}$ alkyl
—N(COCH₂OH)— hydrogen, mono, bis or tris-hydroxy $C_{1-4}$ alkyl
—N(CO—CHOH—CH2OH)— hydrogen, mono, bis or trihydroxylated $C_{1-4}$ alkyl
—N(CO—CHOH—CHOH—CH₂OH)— hydrogen, mono, bis or trihydroxylated $C_{1-4}$ alkyl
—N(COCH₂OH)₂
—CON (CH₂—CHOH—CH₂OH) (CH₂—CH₂OH)
—CONH—C (CH₂OH)₃
—CONH—CH (CH₂OH) (CHOH—CH₂OH) -morpholine-4-carbonyl.

15. The compound as claimed in claim 14 wherein each $R^4$ are the same or different and are selected from groups of the formulas
—CON(CH₃)CH₂—CHOH—CH₂OH, —CONH—CH₂—CHOH—CH₂OH, —CONH—CH—(CH₂OH)₂, —CON—(CH₂—CH₂OH)₂, —CON—(CH₂—CH₂OH—CH₂OH)₂, —NHCOCH₂OH and —N(COCH₂OH)— mono, bis or tris-hydroxy $C_{1-4}$ alkyl.

16. The compound as claimed in claim 1 wherein each $R^4$ are equal.

17. The compound as claimed in claim 16 wherein each $R^4$ denotes —CONH—CH₂—CHOH—CH₂OH.

18. The compound as claimed in claim 1 wherein said compound is N,N'-Bis-(2,3-dihydroxy-propyl)-5-[3(3-{3-[N,N'-bis-(2,3-dihydroxy-propyl)-2,4,6-triiodo-phenyl]-ureido}-2-{3-[N,N'-bis-(2,3-dihydroxy-propyl)-2,4,6-triiodo-phenyl]-ureidomethyl}-2-methyl-propyl)-ureido]-2,4,6-triiodoisophthalamide;

N,N'-Bis-(2,3-dihydroxy-propyl)-5-(3-{3-{3-[3,5-bis-(2,3-dihydroxy-propylcarbamoyl)-2,4,6-triiodo-phenyl]-ureido}-2-hydroxymethyl-2-[3,5-bis-(2,3-dihydroxy-propylcarbamoyl)-2,4,6-triiodo-phenyl]-ureido)-methyl]propyl}-ureido)-2,4,6-triiodo-isophthalamide;

Tris(N,N,N',N'-Tetrakis-(2,3-dihydroxy-propyl)-5-(3,3-dimethyl-ureido)-2,4,6-triiodo-isophthalamide)ethane;

Tris-(ethyl-3-[2,4,6-triiodo-3,5-bis-(morpholine-4-carbonyl)-phenyl]-urea)methane;

Tris-(N,N'-bis-(2,3-dihydroxy-propyl)-5-(3-ethyl-ureido)-2,4,6-triiodo-N,N'-dimethyl-isophthalamide) methane;

Tris(N,N,N',N'-Tetrakis-(2,3-dihydroxy-propyl)-2,4,6-triiodo-5-(3-methyl-3-propyl-ureido)-isophthalamide) methane;

Tris-{3-[3,5-bis-(2,3-dihydroxypropylcarbamoyl)-2,4,6-triiodo-phenylcarbamoyloxy-propyl}methane; or Tris([3,5-Bis-(2,3-dihydroxy-propylcarbamoyl)-2,4,6-triiodo-phenyl]-carbamic acid methyl ester)ethane.

19. A diagnostic composition comprising a compound of formula (I) as defined in claim 1 together with a pharmaceutically acceptable carrier or excipient.

20. A method for aiding diagnosis comprising administration of compounds of formula (I) as defined in claim 1 to the human or animal body, examining the body with a diagnostic device and compiling data from the examination.

* * * * *